US008586943B2

(12) United States Patent
Verbeck, IV et al.

(10) Patent No.: US 8,586,943 B2
(45) Date of Patent: Nov. 19, 2013

(54) PETROLEUM OIL ANALYSIS USING LIQUID NITROGEN COLD STAGE—LASER ABLATION—ICP MASS SPECTROMETRY

(75) Inventors: Guido Fridolin Verbeck, IV, Plano, TX (US); William D. Hoffman, Lewisville, TX (US)

(73) Assignee: University of North Texas, Denton, TX (US)

( * ) Notice: Subject to any disclaimer, the term of this patent is extended or adjusted under 35 U.S.C. 154(b) by 30 days.

(21) Appl. No.: 13/287,686

(22) Filed: Nov. 2, 2011

(65) Prior Publication Data

US 2012/0104244 A1 May 3, 2012

Related U.S. Application Data

(60) Provisional application No. 61/409,868, filed on Nov. 3, 2010.

(51) Int. Cl.
*G01N 1/42* (2006.01)
*H01J 49/26* (2006.01)

(52) U.S. Cl.
USPC ............................ 250/429; 250/428; 250/282

(58) Field of Classification Search
USPC ........... 250/428, 429, 282; 73/863.11, 863.12
See application file for complete search history.

(56) References Cited

U.S. PATENT DOCUMENTS

| 4,335,620 | A | * | 6/1982 | Adams ........................ 73/863.11 |
| 5,033,541 | A | | 7/1991 | D'Silva |
| 6,765,794 | B1 | * | 7/2004 | Inoue ............................ 361/695 |
| 2008/0093543 | A1 | * | 4/2008 | Hersman ...................... 250/251 |
| 2012/0069524 | A1 | * | 3/2012 | Schulz-Harder et al. ..... 361/716 |

* cited by examiner

*Primary Examiner* — David A Vanore
*Assistant Examiner* — Wyatt Stoffa
(74) *Attorney, Agent, or Firm* — Edwin S. Flores; Chainey P. Singleton; Chalker Flores, LLP

(57) ABSTRACT

A novel application of a cold-stage coupled to a laser ablation-ICP-MS system is disclosed herein. The novel system of the present invention offers significant advantages over other systems employed for cooling samples prior to LA-ICP-MS analysis. The system discloses herein has multiple applications, including detection of one or more metal contaminants in an oil sample.

18 Claims, 8 Drawing Sheets

PETROLEUM OIL ANALYSIS USING LIQUID NITROGEN COLD STAGE—LASER ABLATION—ICP MASS SPECTROMETRY

CROSS-REFERENCE TO RELATED APPLICATIONS

This application claims priority to U.S. Provisional Application Ser. No. 61/409,868, filed Nov. 3, 2010, the entire contents of which are incorporated herein by reference.

TECHNICAL FIELD OF THE INVENTION

The present invention relates in general to the field of mass spectrometry (MS), and more particularly to a technique involving cooling oil and petroleum samples using a cold stage and combining it with laser ablation-ICP-MS methodologies to determine metal concentrations in the samples.

STATEMENT OF FEDERALLY FUNDED RESEARCH

None.

INCORPORATION-BY-REFERENCE OF MATERIALS FILED ON COMPACT DISC

None.

REFERENCE TO A SEQUENCE LISTING

None.

BACKGROUND OF THE INVENTION

Without limiting the scope of the invention, its background is described in connection with sample processing methods for laser ablation-ICP-MS analysis.

U.S. Pat. No. 5,033,541 issued to D'silva (1991) discloses a double pass tandem cooling aerosol condenser apparatus for receiving aerosol from a liquid solution for a specimen sample which has been prepared for injection into an inductively coupled plasma associated with an emission spectra or mass spectrometer comprises inner and outer compartments for circulating a coolant there through. The aerosol, comprising solvent and analyte particles, is passed through compartments of the condenser which are interposed between the inner and outer coolant compartment. The temperature of the aerosol compartment is adjusted and controlled such that the solvent particles, which would otherwise quench the inductively coupled plasma, are condensed and stripped from the aerosol leaving a relatively stable, dry aerosol containing the desolvated analyte particles for spectrometric analysis.

SUMMARY OF THE INVENTION

The present invention describes a novel application of cold-stage housing for cooling samples to sub-ambient temperatures before analysis using a laser ablation-ICP-MS system.

In one embodiment the instant invention is an assembly for cooling one or more samples prior to or during laser ablation (LA)-inductively coupled plasma (ICP)-mass spectrometry (MS) comprising: (i) a rectangular metallic housing comprising a front face, a top face, a bottom face and three side faces, wherein the housing encases one or more thermal barrier inserts and thermal conducting plugs, (ii) a circular groove fabricated by drilling on the top face of the housing, wherein the circular groove is an O-ring groove and is fabricated with a specified inner and outer diameter and is also centered at a specified distance from the front face of the housing and the side faces of the housing, (iii) a first hole drilled on the top face of the housing, wherein the first hole is centered on the top face of the housing and traverses half the height of the housing, (iv) a second hole drilled on the front face of the housing, wherein the second hole is centered on the front face of the housing and traverses along a length of the housing and is orthogonal to the first hole, (v) a first thermal barrier insert of a specified length and diameter, wherein the first thermal barrier insert comprises a first insert hole centered from a rear side of the first thermal barrier insert and a second insert hole orthogonal to the first insert hole on a side of the first thermal barrier insert, wherein the first thermal barrier insert is placed inside the second hole drilled on the front face of the housing, (vi) a second thermal barrier insert of a specified length, wherein the second thermal barrier insert comprises a semi-circular cut centered along a base of the second thermal barrier insert, wherein the second thermal barrier insert comprises a hole of a specified diameter traversing an entire length of the second thermal barrier insert, wherein the second thermal barrier insert is placed inside the first hole drilled on the top face of the housing, (vii) a first thermal conducting plug of a specified outer diameter and length, wherein the first thermal conducting plug comprises a first hole and a second hole on a top or bottom surface of the first thermal conducting plug, wherein the first hole and the second hole have a specified diameter and depth and are separated from each other by a specified distance, wherein a third hole is drilled along a length of the first thermal conducting plug orthogonal to the first hole and the second hole, wherein the third hole is capped by soldering a copper plug, wherein the first and the second holes comprise copper tubing silver soldered in place, wherein the first thermal conducting plug is inserted into the first thermal barrier insert, (viii) a second thermal conducting plug mimicking a shape of the second thermal barrier insert, wherein the second thermal conducting plug is inserted into the first second thermal barrier insert, and (ix) one or more holes on the front face of the housing for inserting a platinum resistive temperature device (RTD), a thermocouple, a temperature sensor, resistance temperature detectors or any other suitable temperature monitoring device or a similar device for monitoring a temperature of the assembly.

In one aspect of the assembly hereinabove the method of forming the assembly comprises the steps of: i) inserting the first thermal barrier insert into the second hole drilled on the front face of the housing, ii) fitting the first thermal conducting plug into the first thermal barrier insert, iii) inserting the second thermal barrier insert into the first hole drilled on the top face of the housing, wherein the second thermal barrier insert fits against the first thermal barrier insert, iv) fitting the second thermal conducting plug into the second thermal barrier insert, and v) sealing the assembly by fitting the sealing O-ring in the groove. In another aspect the assembly is fitted inside a laser ablation (LA)-inductively coupled plasma (ICP)-mass spectrometer (MS). In another aspect the metallic housing comprises aluminum, a polymeric material or any other suitable material. In yet another aspect the thermal conducting plug comprises, copper, annealed copper, gold, silver, aluminum, high conductivity metals, and combinations and modifications thereof. In another aspect the thermal barrier insert comprises polystyrene or any other suitable polymeric inserts. In another aspect the sealing O-ring comprises one or more synthetic rubbers or thermoplastics. In a related aspect synthetic rubbers are selected from the group consisting of nitrile, Butadiene rubber (BR), Butyl rubber (IIR), Chlorosulfonated polyethylene (CSM), Epichiorohydrin rubber (ECH, ECO), Ethylene propylene diene monomer (EPDM), Ethylene propylene rubber (EPR), Fluoroelastomer (FKM), Perfluoroelastomer (FFKM), Polyacrylate rubber (ACM), Polychloroprene (CR), Polyisoprene (IR), Polysulfide rubber (PSR), Sanifluor, Silicone rubber (SiR), and Styrene butadiene rubber (SBR). In a specific aspect the sealing O-ring comprises nitrile. In one aspect a cooling in the assembly is performed by flow of liquid nitrogen, liquid oxygen or ethylene glycol, a Peltier cooling device, contact with dry ice or combinations thereof. In another aspect the assembly can achieve and sustain temperatures of 83.6 K or lower. In yet another aspect the assembly is used for an analysis of a level of one or more metals in an oil sample.

In another the instant invention discloses a method for detecting and measuring a level of one or more metals in an oil sample comprising the steps of: (i) providing a laser ablation (LA)-inductively coupled plasma (ICP)-mass spectrometer (MS) system, (ii) fitting a cooling assembly for cooling the oil sample in the LA-ICP-MS system, wherein the cooling assembly comprises: (a) a rectangular metallic housing comprising a front face, a top face, a bottom face and four side faces, wherein the housing encases one or more thermal barrier inserts and thermal conducting plugs, (b) a circular groove fabricated by drilling on the top face, wherein the circular groove is an O-ring groove and is fabricated with a specified inner and outer diameter and is also centered at a specified distance from the front face and the side faces, (c) a first hole drilled on the front face, wherein the hole is centered on the front face and traverses half the height of the housing, (d) a second hole drilled on the front face, wherein the hole is centered on the front face and traverses along a length of the housing and is orthogonal to the first hole, (e) a first thermal barrier insert of a specified length and diameter, wherein the first thermal barrier comprises a first hole centered from a rear side of the insert and a second hole orthogonal to the first hole on a side of the insert, wherein the first insert is placed inside the second hole drilled on the front face, (f) a second thermal barrier insert of a specified length, wherein the second thermal barrier comprises a semi-circular cut centered along a base of the insert, wherein the second thermal barrier insert comprises a hole of a specified diameter traversing an entire length of the insert, wherein the second insert is placed inside the first hole drilled on the top face, (g) a first thermal cylindrical conducting plug of a specified outer diameter and length, wherein the first plug comprises a first and a second holes on a top or bottom surface of a specified diameter and depth and separated from each other by a specified distance, wherein a third hole is drilled along a length of the cylinder orthogonal to the first and the second hole, wherein the third hole is capped by soldering a copper plug, wherein the first and the second holes comprise copper tubing silver soldered in place, wherein the first thermal conducting plug is inserted into the first thermal barrier insert, (h) a second thermal conducting plug mimicking a shape of the second thermal barrier insert; wherein the first thermal conducting plug is inserted into the first thermal barrier insert, and (i) one or more holes on the front face for inserting a platinum resistive temperature device (RTD), a thermocouple, a temperature sensor, resistance temperature detectors or any other suitable temperature monitoring device for monitoring a temperature of the assembly, (iii) creating an inert atmosphere in an ablation chamber of the LA-ICP-MS system by flowing helium, argon or any other suitable inert gas, (iv) decreasing a temperature of the ablation chamber by flowing liquid nitrogen through the cooling assembly, (v) initiating a ablation event once a desired temperature of the cooling assembly is achieved, (vi) generating a mass spectrum following the laser ablation event, and (vii) detecting and measuring a level of one or more metals in an oil sample from the generated mass spectrum.

In one aspect of the method the metallic housing comprises aluminum, a polymeric material or any other suitable material. In another aspect the thermal conducting plug comprises, copper, annealed copper, gold, silver, aluminum, high conductivity metals, and combinations and modifications thereof. In specific aspects the thermal barrier insert comprises polystyrene or any other suitable polymeric inserts and the sealing O-ring comprises nitrile rubber. In yet another aspect a cooling in the assembly is performed by flow of liquid nitrogen, liquid oxygen or ethylene glycol, a Peltier cooling device, contact with dry ice or combinations thereof and the assembly can achieve and sustain temperatures of 83.6 K or lower.

In yet another embodiment the instant invention discloses an assembly for cooling one or more oil samples prior to or during laser ablation (LA)-inductively coupled plasma (ICP)-mass spectrometry (MS) comprising: a rectangular aluminum housing comprising a front face, a top face, a bottom face and four side faces, wherein the aluminum housing encases one or more polymeric thermal barrier inserts and copper thermal conducting plugs.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
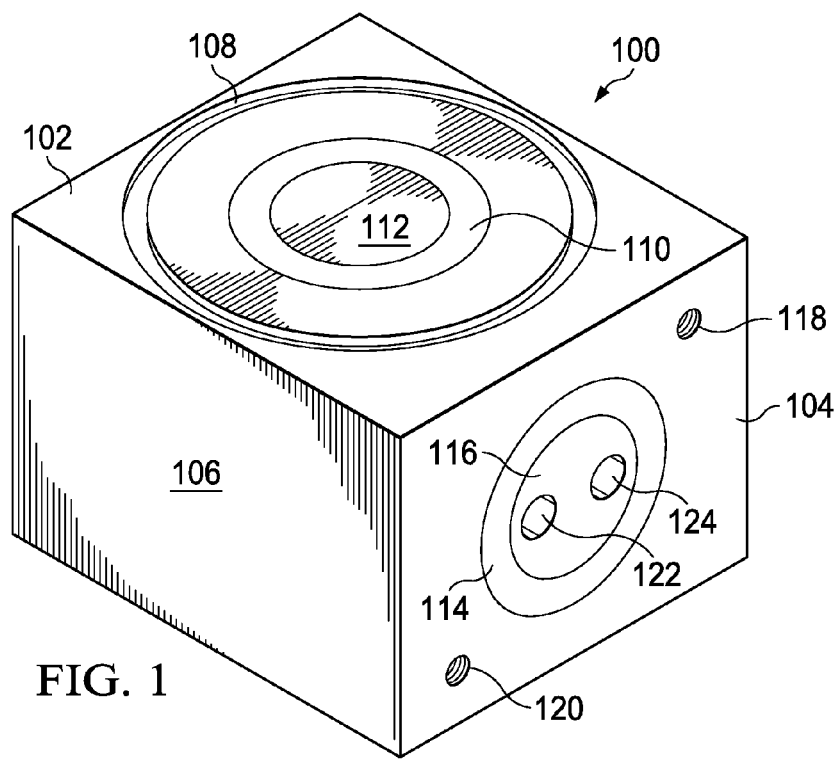
FIG. 1 is a schematic showing the cold stage assembly of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The terms "mass spectrometry" or "MS" as used herein refer to methods of filtering, detecting, and measuring ions based on their mass-to-charge ratio or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety.

The term "inductively coupled plasma" as used herein refers to methods in which a sample is interacted with a partially ionized gas at a sufficiently high temperature to atomize and ionize most elements.

The term "laser ablation" refers to the evaporation or removal of the target material by the focused energy of the laser beam. The bulk target material is converted into vapor components of atoms, ions, clusters, and particles. These vapor components are collected on the heated substrate and form a thin film.

The "Inductively coupled plasma mass spectrometry (ICP-MS)" refers to a type of mass spectrometry that is highly sensitive and capable of the determination of a range of metals and several non-metals at concentrations below one part in $10^{12}$ (part per trillion). It is based on coupling together an inductively coupled plasma capable of producing ions (ionization) with a mass spectrometer capable of separating and detecting the ions.

The present invention is a novel application of a cold-stage to a laser ablation (LA)-inductively coupled plasma (ICP)-mass spectrometry system (MS) system. The cold stage described herein is comprised of two orthogonal copper slugs in thermal contact, with liquid nitrogen flowing through one of the slugs. The housing is inserted into a LA system coupled to an ICP-MS followed by initiation of the ablation and collection of the MS data.

Recent developments have greatly enhanced the spatial resolution available in LA-ICP-MS. These developments have made it desirable to utilize this technique for surface sampling of specimens that would not normally suit laser ablation techniques. The present inventors have designed and implemented a cold stage capable of cooling samples to sub-ambient temperatures prior to analyses with the primary focus on studying oil based samples. Oil based samples are of particular interest because of the inherent suitability of ICP-MS methodologies to determine metal concentrations very accurately. The cold stage is comprised of two orthogonal copper slugs in thermal contact. Liquid nitrogen is flowed through one of the slugs to generate the desired temperature. These slugs are housed in Rexolite inserts, which are then encased in an aluminum housing. Temperature is measured by a Lakeshore platinum resistance temperature detector. The system described herein can sustain temperatures as low as 83.6 K with a constant liquid nitrogen flow.

Typical analysis proceeds as focusing on the specimen in question, cooling the stage to the desired temperature, and initiating the ablation/detection event. Bringing the samples down to liquid nitrogen temperatures decreases the degrees of freedom available for the samples to dissipate the 213 nm radiation. Though the system described herein uses a 213 nm radiation, it will be apparent to those of skill in the art that the method of the present invention would be applicable to systems using any wavelength of incident radiation. Cooling the oil based samples has significant advantages because of the consistency of the ablation event. Additionally, lower laser powers can be used to generate similar ablation efficiencies and may have the added benefit of decreasing the extent of preferential fractionation. Utilizing the cold stage eliminates the cumbersome step of developing matrix matched standards which are suitable for consistent laser ablation at ambient temperatures and may reduce matrix effects that interfere with analytes.

Current ICP-MS systems require an oxygen source to analyze organic compounds, thereby adding another level of gas phase chemistry to the process. The instant invention eliminates the added steps, and makes direct analysis possible.

The device described herein has a cold touch (typically copper or equally conductive material), a method of cooling (liquid nitrogen flow tube), a way of monitoring the cooling and maintaining optimal He, Ar or other inert gas flow rate at variable temperatures. The cooling in the present invention is performed by a Peltier device, a liquid flow (liquid nitrogen, ethylene glycol, etc.) or contact cooling (as dry ice).

FIG. 1 is a schematic showing the cold stage assembly. The stage housing comprises an aluminum body 100 encasing the thermal barrier inserts (110 and 114) as well as the thermal conducting plugs (112 and 116). The aluminum body 100 is a rectangular prism measuring 2.90" wide, 2.17" tall, and 3.20" deep. The aluminum body 100 has a top face 102, a front face 104, a bottom face (not shown in FIG. 1), and three other side faces (one of which is shown in FIG. 1 as side face 106). An o-ring groove 108 is formed in the top face 102 measuring 2.79" outside diameter, 2.49" inside diameter and 0.12" deep and is centered at 1.75" from the front face 104 of the housing 100 and 1.45" from the side. At this same point on the top face 102, a first 1.50" hole is drilled half the height of the aluminum housing 100 (1.085"). Through the front face 104 a second 1.50" hole is drilled orthogonal to the first 1.50" hole and the second hole 1.50" hole traverses from front to back. This second 1.50" hole is centered on the front face 104. A first threaded hole 118 and a second threaded hole 120 are formed in the front face 104 to receive a bolt 222 and a bolt 224 (shown in FIGS. 2A and 2B) fasten a thin pressure plate (not shown) to contain a thermal conducting plug 116. The thermal barrier inserts (110 and 114) are composed of a material with a low thermal expansion coefficient as well as a suitably low minimum working temperature. The lack of moving parts negates the need for a high mechanical stress material. The preferred material is Rexolite, but any suitable material may be substituted. The thermal barrier inserts (110 and 114) are two separate parts. Insert 114 is the insert that traverses the fore-to-aft segment of the housing. It is 3.20" long and 1.495" in diameter. A first 1.00" hole through insert 114 is centered on the front face of insert 114 to allow for insertion of the thermal conducting plug 116. Orthogonal to this first 1.00" hole is a second 1.00" diameter hole centered 1.748" from the rear of the thermal barrier insert 114 and 0.7475" from the side of the thermal barrier insert 114. Thermal barrier insert 110 is 1.08" tall with a semi-circular cut removed from its base. This semi-circular cut is of radius 0.75" and originates at the bottom edge of the thermal barrier insert 110 and is centered along it. This thermal barrier insert 110 is also equipped with a 1.0" diameter hole through the thermal barrier insert 110. Thermal barrier insert 110 has a 1.495" outside diameter. Thermal conducting plug 116 is 0.995" outside diameter and 3.20" long. Thermal conducting plug 116 is equipped with two 0.25" holes (122 and 124) that are 2.725" deep. These holes (122 and 124) are spaced 0.13" from the edge of thermal conducting plug 116 and 0.50" apart from one another. At 2.60" along the length of the thermal conducting plug 116 is another ¼" hole orthogonal to the other two. This hole is 0.875" deep so as to connect the holes drilled along the length of the plug. This connecting hole is capped with a ¼" copper plug 0.13" thick that is soldered in place. The two holes 122 and 124 along the length of the plug were also fitted with lengths of ¼" copper tubing silver soldered in place. Thermal conducting plug 112 mimics the shape of thermal barrier insert 110 but there is no through hole drilled in position. Both thermal conducting plugs (112 and 116) should be of a material that allows sufficient transfer of the thermal energy from the sample out to the cooling medium. The preferred embodiment is copper for these plugs, but any similar high conductivity metal may be substituted. Both of the thermal conducting plugs (112 and 116) should be 0.995" in outside diameter. The sealing o-ring 108 should be of a material capable of maintaining sealing properties at least as low as the desired analysis temperature. Nitrile has been used successfully by the inventors. Assembly proceeds as thermal barrier insert 114 is inserted into the aluminum housing 100, and subsequently thermal conducting plug 116 is fitted into thermal barrier insert 114. Following these steps, thermal barrier insert 110 is inserted to fit against thermal barrier insert 114. Similarly, thermal conducting plug 112 is inserted in thermal barrier insert 110. Finally, the o-ring 108 was fitted in the groove for sealing. Though the dimensions described hereinabove represent the size of the system used by the present inventors, it will be apparent to those skilled in the art that this stage could be built to be any size to accommodate the desired sample. Generally, this stage would be significantly inefficient when built to larger scales, but in the range of 2-6 inches for the aluminum body 100 would be generally useful and accepted. In addition, the dimensions of the thermal conducting media and the thermal insulating media may be altered so as to accommodate the samples, but in general 0.25-4 inches would be useful.

Figure 2A:
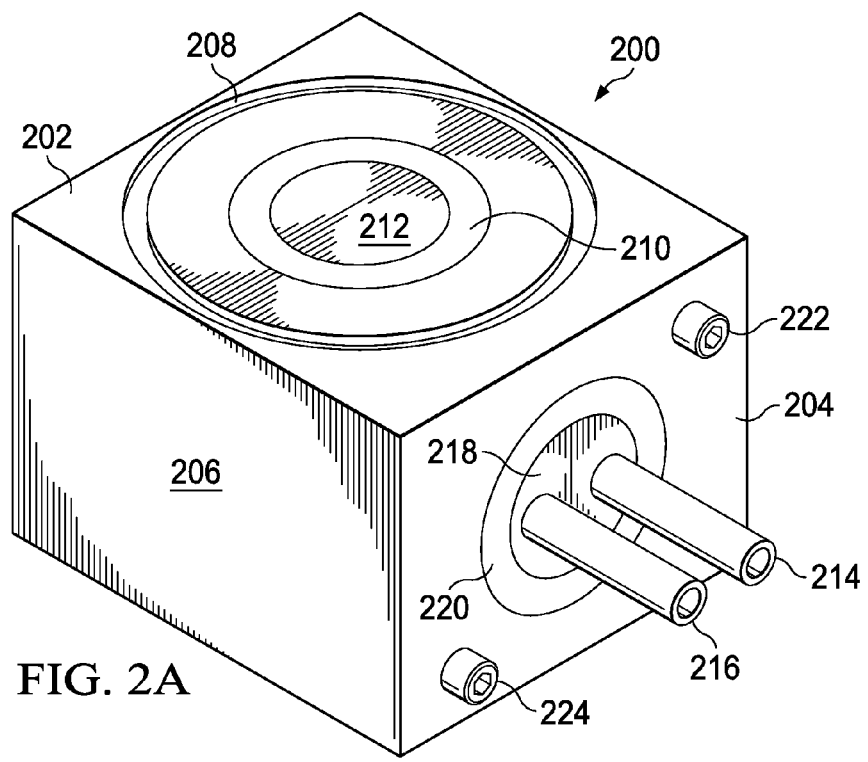
FIGS. 2A-2B are images showing the cold stage assembly (FIG. 2A) and its individual components (FIG. 2B)
Figure 2B:
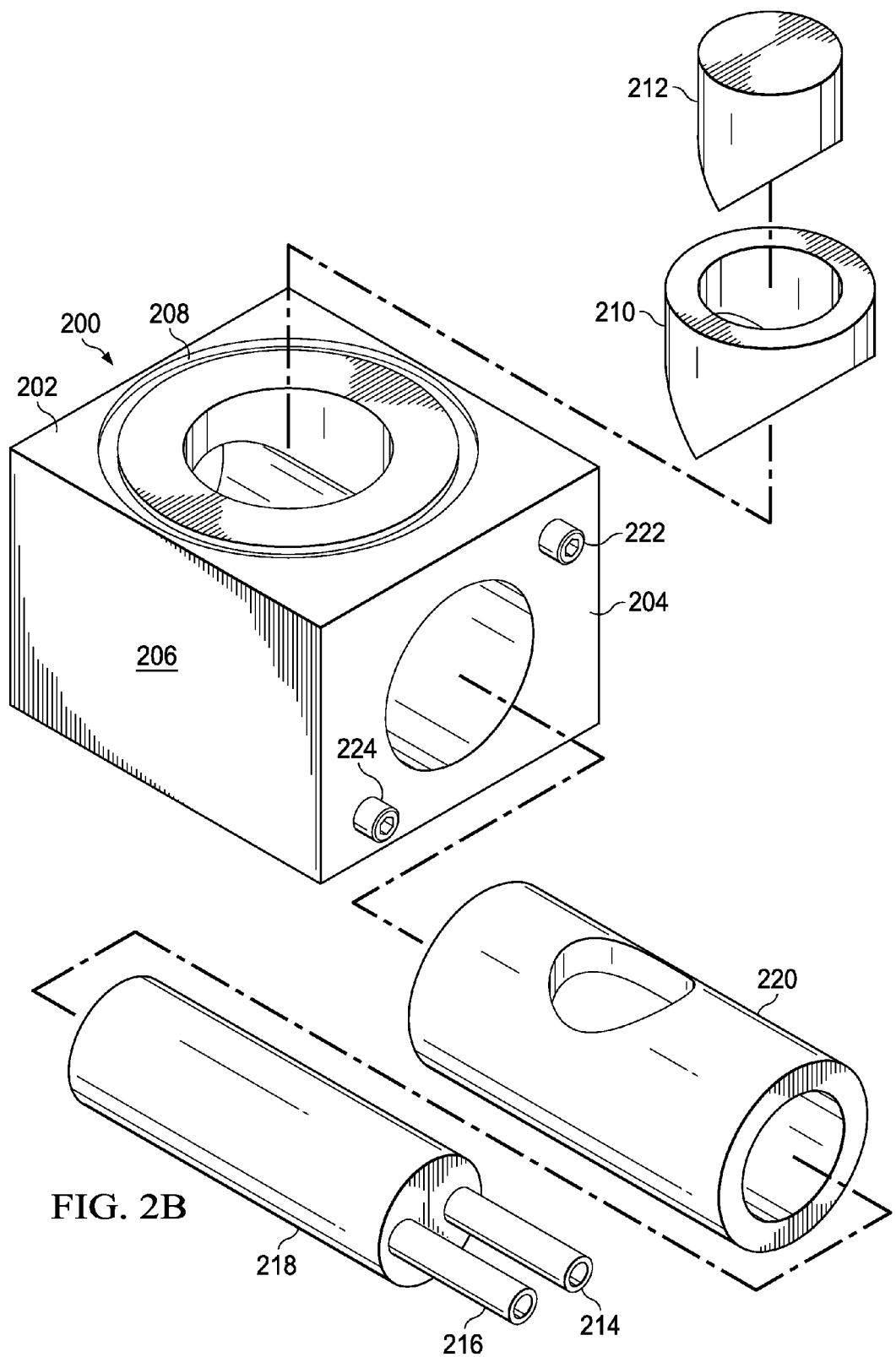

FIG. 2A is a photographic image of the image of the cold-stage assembly, the individual components of which are shown in FIG. 2B.

As shown in FIG. 2A and in FIG. 2B, the stage housing comprises an aluminum body 200 encasing the thermal barrier inserts (210 and 220) as well as the thermal conducting plugs (212 and 218). The aluminum body 200 is a rectangular prism measuring 2.90" wide, 2.17" tall, and 3.20" deep. The aluminum body 200 has a top face 202, a front face 204, a bottom face (not shown in FIG. 2A or in FIG. 2B), and three other side faces (one of which is shown in FIG. 2A and in FIG. 2B as side face 206). An o-ring groove 208 is formed in the top face 202 measuring 2.79" outside diameter, 2.49" inside diameter and 0.12" deep and is centered at 1.75" from the front face 204 of the housing 200 and 1.45" from the side. At this same point on the top face 202, a first 1.50" hole is drilled half the height of the aluminum housing 100 (1.085"). Through the front face 204 a second 1.50" hole is drilled orthogonal to the first 1.50" hole and the second hole 1.50" hole traverses from front to back. This second 1.50" hole is centered on the front face 204. A first bolt 222 and a second bolt 224 are inserted in holes (not shown) in the front face 204 to fasten a thin pressure plate (not shown) to contain a thermal conducting plug 218. The thermal barrier inserts (210 and 220) are composed of a material with a low thermal expansion coefficient as well as a suitably low minimum working temperature. The lack of moving parts negates the need for a high mechanical stress material. The preferred material is Rexolite, but any suitable material may be substituted. The thermal barrier inserts (210 and 220) are two separate parts. Insert 220 is the insert that traverses the fore-to-aft segment of the housing. It is 3.20" long and 1.495" in diameter. A first 1.00" hole through insert 220 is centered on the front face of insert 220 to allow for insertion of the thermal conducting plug 218. Orthogonal to this first 1.00" hole is a second 1.00" diameter hole centered 1.748" from the rear of the thermal barrier insert 220 and 0.7475" from the side of the thermal barrier insert 220. Thermal barrier insert 210 is 1.08" tall with a semi-circular cut removed from its base. This semi-circular cut is of radius 0.75" and originates at the bottom edge of the thermal barrier insert 210 and is centered along it. This thermal barrier insert 210 is also equipped with a 1.0" diameter hole through the thermal barrier insert 210. Thermal barrier insert 210 has a 1.495" outside diameter. Thermal conducting plug 218 is 0.995" outside diameter and 3.20" long. Thermal conducting plug 218 is equipped with two conduits holes (214 and 216). These two conduits holes (214 and 216) are spaced 0.13" from the edge of thermal conducting plug 218 and 0.50" apart from one another. At 2.60" along the length of the thermal conducting plug 218 is another ¼" hole orthogonal to the other two. This hole is 0.875" deep so as to connect the holes drilled along the length of the plug. This connecting hole is capped with a ¼" copper plug 0.13" thick that is soldered in place. The two conduits 214 and 216 along the length of the plug are fitted with lengths of ¼" copper tubing silver soldered in place. Thermal conducting plug 212 mimics the shape of thermal barrier insert 210 but there is no through hole drilled in position. Both thermal conducting plugs (212 and 218) should be of a material that allows sufficient transfer of the thermal energy from the sample out to the cooling medium. The preferred embodiment is copper for these plugs, but any similar high conductivity metal may be substituted. Both of the thermal conducting plugs (212 and 218) should be 0.995" in outside diameter. The sealing o-ring 208 should be of a material capable of maintaining sealing properties at least as low as the desired analysis temperature. Nitrile has been used successfully by the inventors. Assembly proceeds as thermal barrier insert 220 is inserted into the aluminum housing 200, and subsequently thermal conducting plug 218 is fitted into thermal barrier insert 220. Following these steps, thermal barrier insert 210 is inserted to fit against thermal barrier insert 220. Similarly, thermal conducting plug 212 is inserted in thermal barrier insert 210. Finally, the o-ring 208 was fitted in the groove for sealing. Though the dimensions described hereinabove represent the size of the system used by the present inventors, it will be apparent to those skilled in the art that this stage could be built to be any size to accommodate the desired sample. Generally, this stage would be significantly inefficient when built to larger scales, but in the range of 2-6 inches for the aluminum body 200 would be generally useful and accepted. In addition, the dimensions of the thermal conducting media and the thermal insulating media may be altered so as to accommodate the samples, but in general 0.25-4 inches would be useful.

Figure 3A:
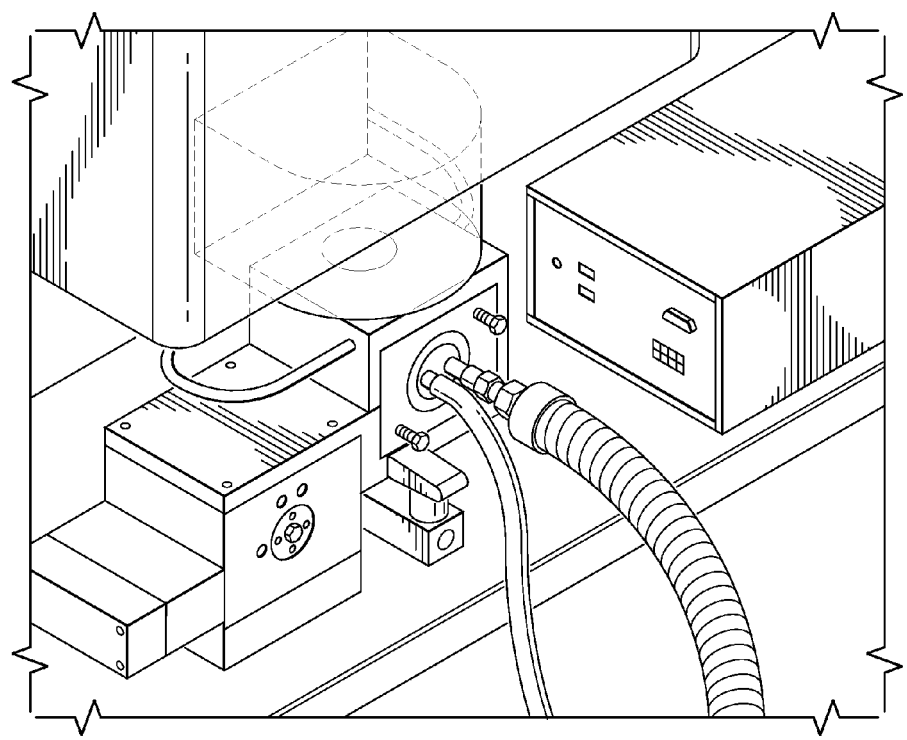
FIGS. 3A and 3B shows the combined cold stage laser ablation-ICP-MS set-up according an embodiment of the present invention.
Figure 3B:
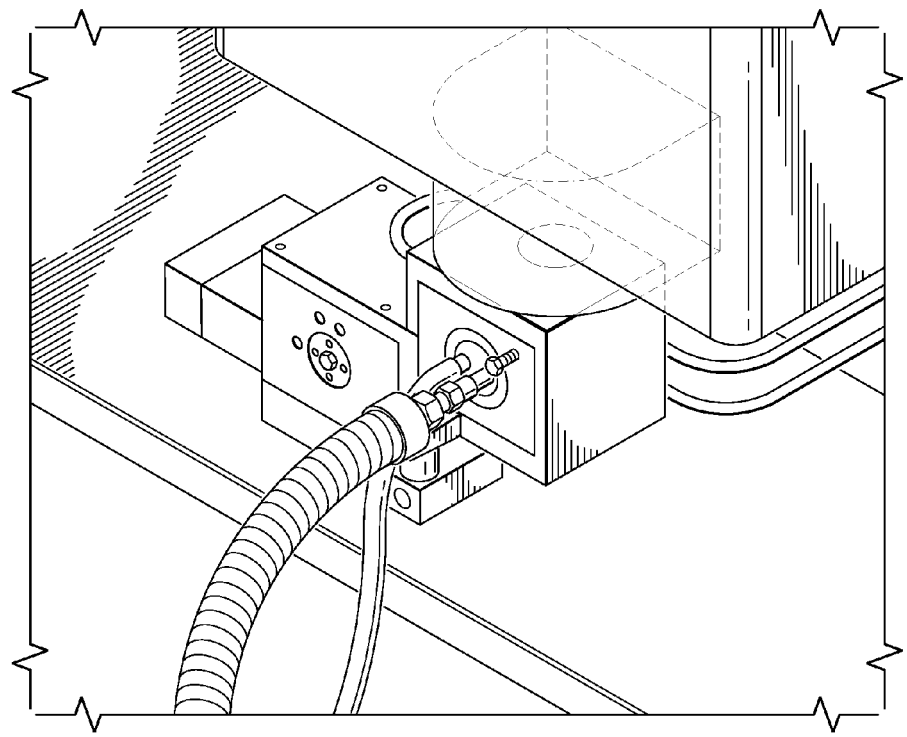
Figure 4:
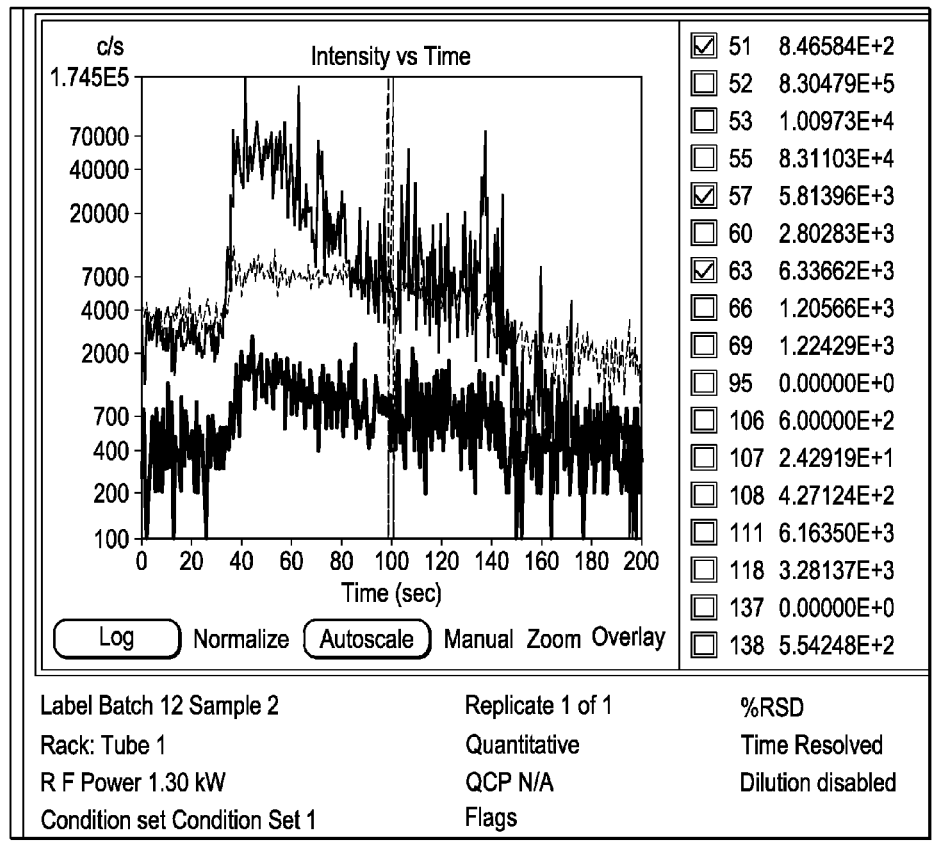
FIG. 4 is a readout showing the results of a metal analysis performed on a oil sample using the cold-stage described in the present invention. The analysis was completed at 200 K.

FIGS. 3A and 3B are images showing the combined cold stage laser ablation-ICP-MS set-up according an embodiment of the present invention. Analyses proceeds by inserting the housing into the laser ablation system. The desired area of the sample is focused and a pattern is established for laser ablation analyses utilizing commercially available laser ablation software. Subsequently, the ablation chamber is purged with a flow of helium gas, and this flow is established into the online mode of the ICP-MS. Though, helium was used by the present inventors, it is not a requirement any inert carrier gas (e.g. argon, nitrogen, etc.) can be used. Once under an inert atmosphere of helium gas, the temperature is decreased by flowing liquid nitrogen or liquid oxygen through thermal conducting insert 1 until the desired temperature is realized; once the desired temperature for analysis has been reached, the ablation event is initiated and ICP-MS data is collected. For example, FIG. 4 is a readout showing the results of a metal analysis performed on a oil sample using the cold-stage described in the present invention. The analysis was completed at 200 K. This system has recorded sustained temperatures as low as 83.6 K with a constant flow of liquid nitrogen. Temperature may be monitored by a platinum resistive temperature device (RTD) (or a thermocouple, a temperature sensor, resistance temperature detectors or any other suitable temperature monitoring device) placed in auxiliary hole in thermal conducting plug 1. Though the materials presented above are the most desirable, any suitable materials may be used to construct the housing, thermal conducting inserts and the thermal insulating inserts of the present invention. Temperature measurement may be completed by any suitable system capable of recording temperatures from ambient to cryogenic. In the system of the present invention, temperature measurement is carried out by a platinum RTD connected to a temperature recording device using the 4-wire method of connection.

Figure 5:
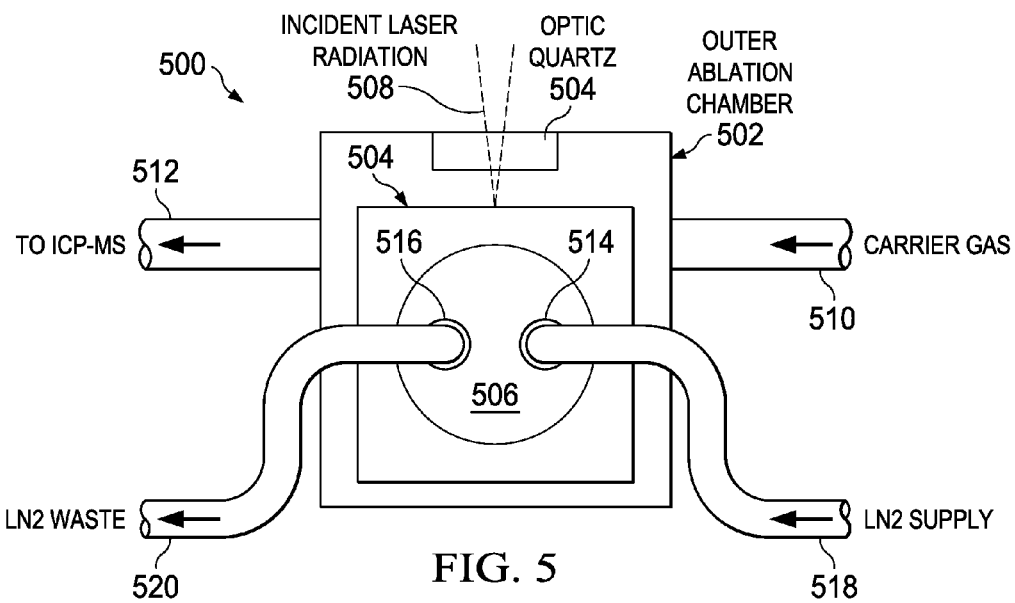
FIG. 5 is a schematic representation of the experimental setup for completing sub-ambient laser ablation sampling of oil based samples.

A schematic representation of the experimental setup 500 for completing sub-ambient laser ablation sampling of oil based samples FIG. 5. The system 500 comprises and outer and inner ablation chamber 502 and 504, respectively. A cold-stage assembly 506 is placed in the inner chamber 504. The assembly has an inlet (or a supply line) 518 for introduction of the oil sample and an outlet line 520 for removal of the waste. A carrier gas is introduced through inlet 508 and the ablated sample is taken to the attached or combined ICP-MS system through an outlet 512. An opening to receive a laser 508 from a source to ablate the introduced sample is provided in the outer chamber 502.

Figure 6A:
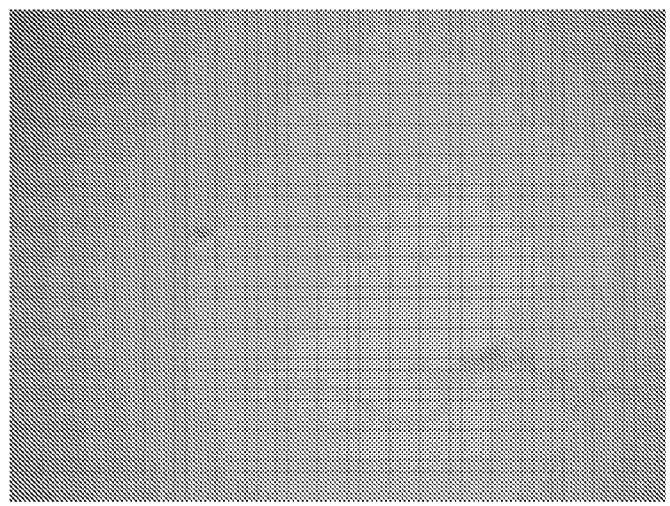
FIGS. 6A and 6B are images demonstrating the visible difference between sample ablation occurring at room temperature (FIG. 6A) and 200 K (FIG. 6B) on a standard oil solution.
Figure 6B:
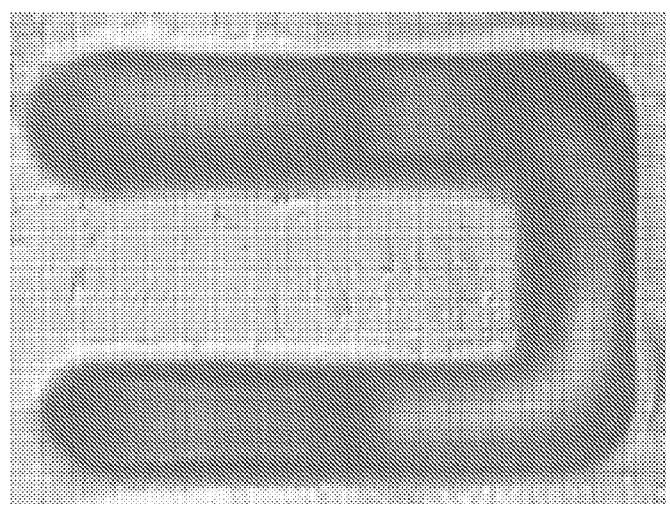
Figure 7:
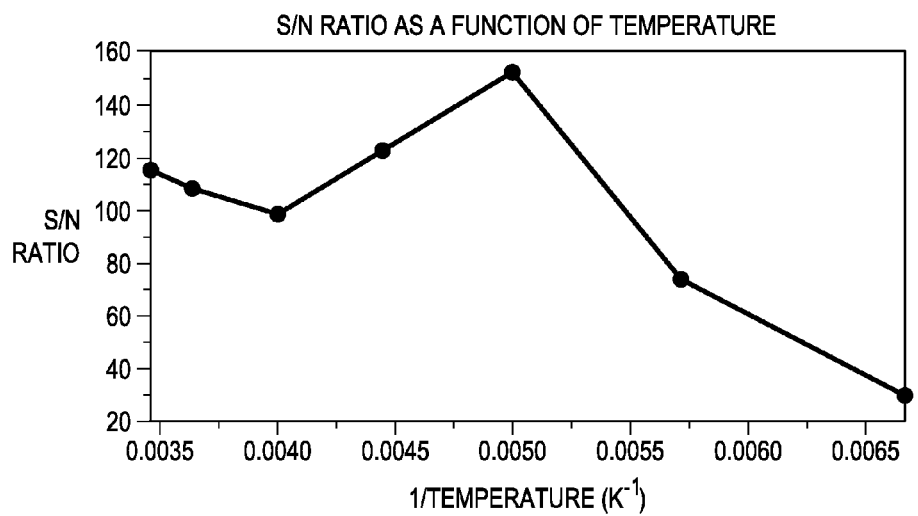
FIG. 7 is a plot showing the relationship between signal/noise (S/N) ratio as a function of the temperature.

FIGS. 6A and 6B are images demonstrating the visible difference between sample ablation occurring at room temperature (FIG. 6A) and 200 K (FIG. 6B) on a standard oil solution; There is significant improvement of the appearance of the ablation event at sub-ambient temperatures, allowing oil based samples to be more efficiently ablated. FIG. 7 is a plot showing the relationship between signal/noise (S/N) ratio as a function of the temperature. As the temperature is varied, the signal to noise ratio begins to increase as the sample reaches its freezing point indicating significantly lower detection and quantitation limits at decreased temperatures.

Figure 8A:
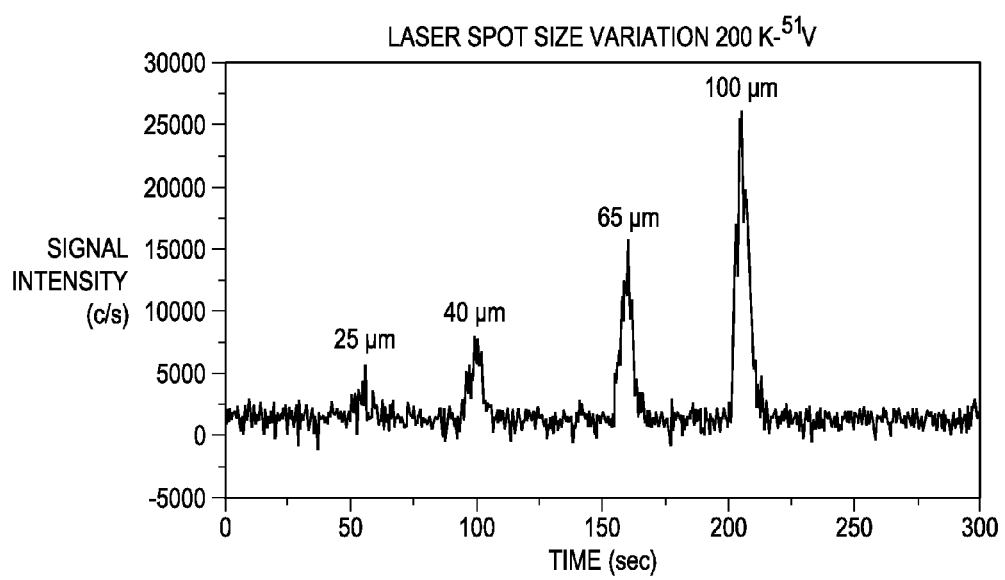
FIGS. 8A and 8B are plots showing the signal from Vanadium-51 as a function of spot size as a function of temperature at 200 K (FIG. 8A) and at room temperature, i.e., 289 K (FIG. 8B)
Figure 8B:
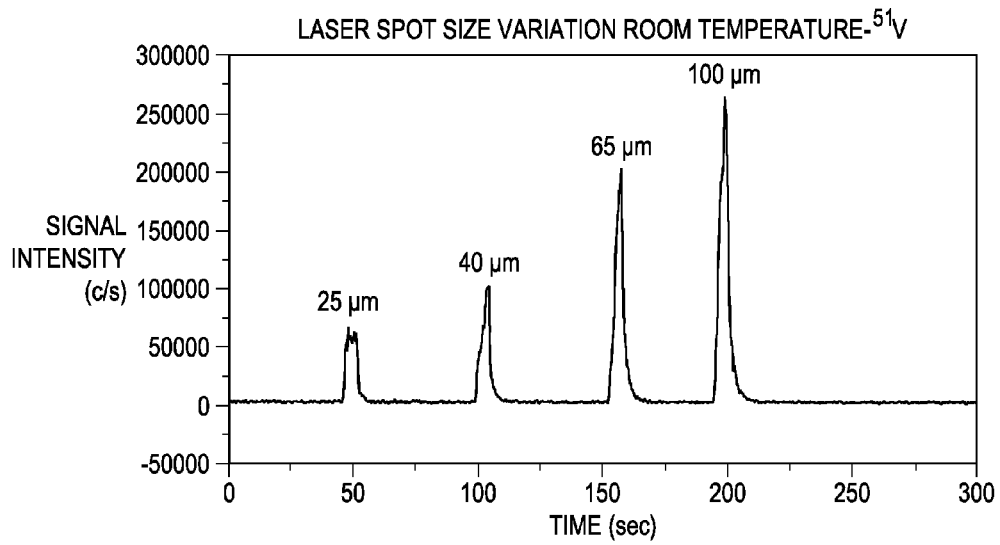

FIGS. 8A and 8B are plots showing the signal from Vanadium-51 as a function of spot size as a function of temperature at 200 K and at room temperature, i.e., 289 K (FIG. 8B), respectively.

Figure 9A:
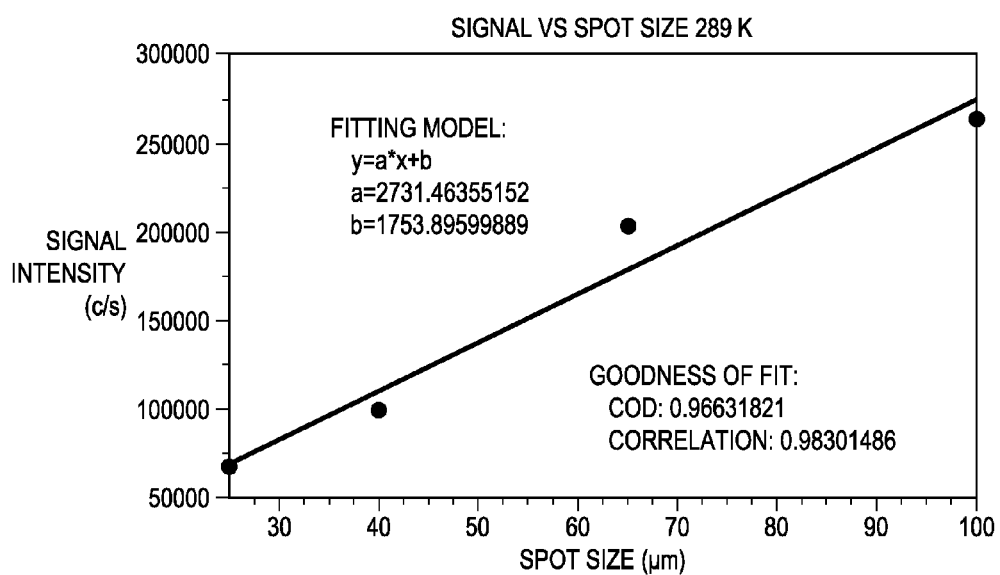
FIGS. 9A and 9B are plots showing the linearity of signal as a function of laser spot size for the sample ablated at room temperature, i.e., 289 K (FIG. 9A) and at 200 K (FIG. 9B).
Figure 9B:
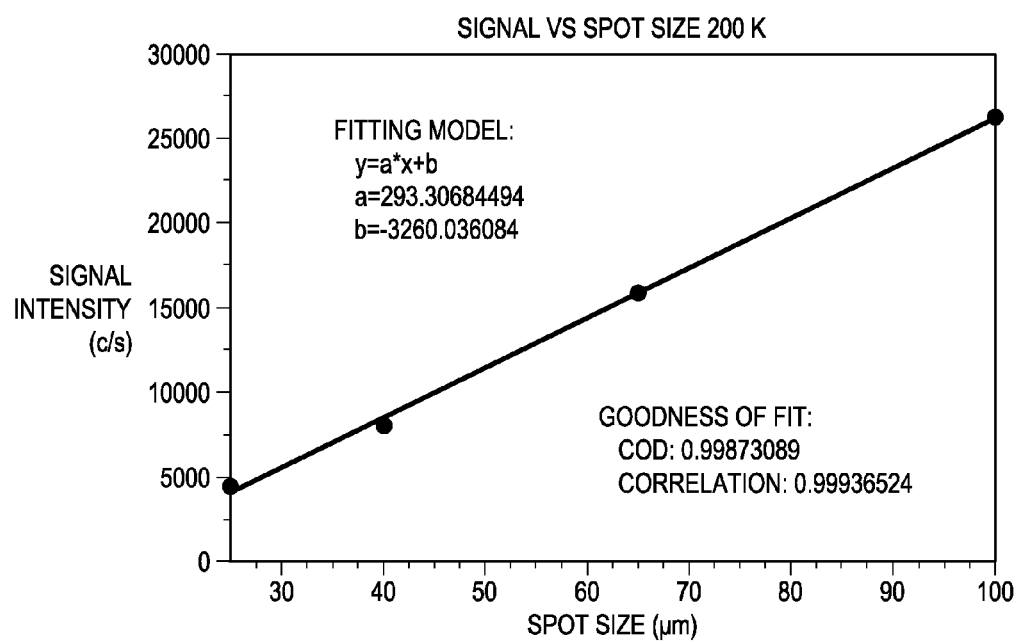

FIG. 9A demonstrates the linearity of signal as a function of laser spot size for the sample ablated at room temperature. The data is significantly non-linear, indicating that there is little correlation between laser spot size and measured signal at ambient temperatures. The linearity of the measured signal as a function of spot size measured at 200 K is shown in FIG. 9B. This data indicates that there is a significantly linear relationship between spot size and signal at sub-ambient temperatures allowing for greater correlation of laser spot size to metal content when compared to typical ambient analyses. A linear relationship allows for the accurate determination of the metal content at various laser spot sizes while retaining spatial resolution on the surface of the sample. This will allow for the investigation of surface inclusions of varying sizes while maintaining the ability to correlate the signal generated to an accurate metal content.

It is contemplated that any embodiment discussed in this specification can be implemented with respect to any method, kit, reagent or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C or combinations thereof" is intended to include at least one of: A, B, C, AB, AC, BC or ABC, and if order is important in a particular context, also BA, CA, CB, CBA, BCA, ACB, BAC or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 5,033,541: Double Pass Tandem Cooling Aerosol Condenser.

What is claimed is:

1. An assembly for cooling one or more samples prior to or during laser ablation (LA)-inductively coupled plasma (ICP)-mass spectrometry (MS) comprising:

a rectangular metallic housing comprising a front face, a top face, a bottom face and three side faces, wherein the housing encases one or more thermal barrier inserts and thermal conducting plugs;

a circular groove fabricated by drilling on the top face of the housing, wherein the circular groove is an O-ring groove and is fabricated with a specified inner and outer diameter and is also centered at a specified distance from the front face of the housing and the side faces of the housing;

a first hole drilled on the top face of the housing, wherein the first hole is centered on the top face of the housing and traverses half the height of the housing;

a second hole drilled on the front face of the housing, wherein the second hole is centered on the front face of the housing and traverses along a length of the housing and is orthogonal to the first hole;

a first thermal barrier insert of a specified length and diameter, wherein the first thermal barrier insert comprises a first insert hole centered from a rear side of the first thermal barrier insert and a second insert hole orthogonal to the first insert hole on a side of the first thermal barrier insert, wherein the first thermal barrier insert is placed inside the second hole drilled on the front face of the housing;

a second thermal barrier insert of a specified length, wherein the second thermal barrier insert comprises a semi-circular cut centered along a base of the second thermal barrier insert, wherein the second thermal barrier insert comprises a hole of a specified diameter traversing an entire length of the second thermal barrier insert, wherein the second thermal barrier insert is placed inside the first hole drilled on the top face of the housing;

a first thermal conducting plug of a specified outer diameter and length, wherein the first thermal conducting plug comprises a first hole and a second hole on a top or bottom surface of the first thermal conducting plug, wherein the first hole and the second hole have a specified diameter and depth and are separated from each other by a specified distance, wherein a third hole is drilled along a length of the first thermal conducting plug orthogonal to the first hole and the second hole, wherein the third hole is capped by soldering a copper plug, wherein the first and the second holes comprise copper tubing silver soldered in place, wherein the first thermal conducting plug is inserted into the first thermal barrier insert;

a second thermal conducting plug mimicking a shape of the second thermal barrier insert; wherein the second thermal conducting plug is inserted into the second thermal barrier insert; and one or more holes on the front face of the housing for inserting a platinum resistive temperature device (RTD), a thermocouple, a temperature sensor, resistance temperature detectors or any other temperature monitoring device or a similar device for monitoring a temperature of the assembly.

2. The assembly of claim 1, wherein the assembly is formed by a method comprising the steps of:

inserting the first thermal barrier insert into the second hole drilled on the front face of the housing;

fitting the first thermal conducting plug into the first thermal barrier insert;

inserting the second thermal barrier insert into the first hole drilled on the top face of the housing, wherein the second thermal barrier insert fits against the first thermal barrier insert;

fitting the second thermal conducting plug into the second thermal barrier insert; and sealing the assembly by fitting the sealing O-ring in the groove.

3. The assembly of claim 1, wherein the assembly is fitted inside a laser ablation (LA)-inductively coupled plasma (ICP)-mass spectrometer (MS).

4. The assembly of claim 1, wherein the metallic housing comprises aluminum, a polymeric material or any other material.

5. The assembly of claim 1, wherein the thermal conducting plug comprises, copper, annealed copper, gold, silver, aluminum, metals, and combinations and modifications thereof.

6. The assembly of claim 1, wherein the thermal barrier insert comprises polystyrene or any other polymeric inserts.

7. The assembly of claim 1, wherein the sealing O-ring comprises one or more synthetic rubbers or thermoplastics.

8. The assembly of claim 7, wherein the synthetic rubbers are selected from the group consisting of nitrile, Butadiene rubber (BR), Butyl rubber (IIR), Chlorosulfonated polyethylene (CSM), Epichlorohydrin rubber (ECH, ECO), Ethylene propylene diene monomer (EPDM), Ethylene propylene rubber (EPR), Fluoroelastomer (FKM), Perfluoroelastomer (FFKM), Polyacrylate rubber (ACM), Polychloroprene (CR), Polyisoprene (IR), Polysulfide rubber (PSR), Sanifluor, Silicone rubber (SiR), and Styrene butadiene rubber (SBR).

9. The assembly of claim 1, wherein the sealing O-ring comprises nitrile.

10. The assembly of claim 1, wherein a cooling in the assembly is performed by flow of liquid nitrogen or ethylene glycol, a Peltier cooling device, contact with dry ice or combinations thereof.

11. The assembly of claim 1, wherein the assembly can achieve and sustain temperatures of 83.6 K or lower.

12. A method for detecting and measuring a level of one or more metals in an oil sample comprising the steps of:
- providing a laser ablation (LA)-inductively coupled plasma (ICP)-mass spectrometer (MS) system;
- fitting a cooling assembly for cooling the oil sample in the LA-ICP-MS system, wherein the cooling assembly comprises:
- a rectangular metallic housing comprising a front face, a top face, a bottom face and three side faces, wherein the housing encases one or more thermal barrier inserts and thermal conducting plugs;
- a circular groove fabricated by drilling on the top face of the housing, wherein the circular groove is an O-ring groove and is fabricated with a specified inner and outer diameter and is also centered at a specified distance from the front face of the housing and the side faces of the housing;
- a first hole drilled on the top face of the housing, wherein the first hole is centered on the top face of the housing and traverses half the height of the housing;
- a second hole drilled on the front face of the housing, wherein the second hole is centered on the front face of the housing and traverses along a length of the housing and is orthogonal to the first hole;
- a first thermal barrier insert of a specified length and diameter, wherein the first thermal barrier insert comprises a first insert hole centered from a rear side of the first thermal barrier insert and a second insert hole orthogonal to the first insert hole on a side of the first thermal barrier insert, wherein the first thermal barrier insert is placed inside the second hole drilled on the front face of the housing;
- a second thermal barrier insert of a specified length, wherein the second thermal barrier insert comprises a semi-circular cut centered along a base of the second thermal barrier insert, wherein the second thermal barrier insert comprises a hole of a specified diameter traversing an entire length of the second thermal barrier insert, wherein the second thermal barrier insert is placed inside the first hole drilled on the top face of the housing;
- a first thermal conducting plug of a specified outer diameter and length, wherein the first thermal conducting plug comprises a first hole and a second hole on a top or bottom surface of the first thermal conducting plug, wherein the first hole and the second hole have a specified diameter and depth and are separated from each other by a specified distance, wherein a third hole is drilled along a length of the first thermal conducting plug orthogonal to the first hole and the second hole, wherein the third hole is capped by soldering a copper plug, wherein the first and the second holes comprise copper tubing silver soldered in place, wherein the first thermal conducting plug is inserted into the first thermal barrier insert;
- a second thermal conducting plug mimicking a shape of the second thermal barrier insert; wherein the second thermal conducting plug is inserted into the second thermal barrier insert; and
- one or more holes on the front face of the housing for inserting a platinum resistive temperature device (RTD), a thermocouple, a temperature sensor, resistance temperature detectors or any other temperature monitoring device for monitoring a temperature of the assembly;
- creating an inert atmosphere in an ablation chamber of the LA-ICP-MS system by flowing helium, argon or any other inert gas;
- decreasing a temperature of the ablation chamber by flowing liquid nitrogen through the cooling assembly;
- initiating a ablation event once a desired temperature of the cooling assembly is achieved;
- generating a mass spectrum following the laser ablation event; and
- detecting and measuring a level of one or more metals in an oil sample from the generated mass spectrum.

13. The method of claim 12, wherein the metallic housing comprises aluminum, a polymeric material or any other material.

14. The method of claim 12, wherein the thermal conducting plug comprises, copper, annealed copper, gold, silver, aluminum, metals, and combinations and modifications thereof.

15. The method of claim 12, wherein the thermal barrier insert comprises polystyrene or any other polymeric inserts.

16. The method of claim 12, wherein the sealing O-ring comprises nitrile rubber.

17. The method of claim 12, wherein a cooling in the assembly is performed by flow of liquid nitrogen, liquid oxygen or ethylene glycol, a Peltier cooling device, contact with dry ice or combinations thereof.

18. The method of claim 12, wherein the assembly can achieve and sustain temperatures of 83.6 K or lower.

* * * * *